(12) United States Patent
Segelman

(10) Patent No.: US 6,187,313 B1
(45) Date of Patent: Feb. 13, 2001

(54) **COMPOSITION AND METHOD FOR TREATING AND PREVENTING *HELICOBACTOR-PYLORI*-ASSOCIATED STOMACH GASTRITIS, ULCERS AND CANCER**

(75) Inventor: Alvin Burton Segelman, Orem, UT (US)

(73) Assignee: Nature's Sunshine Products, Inc., Provo, UT (US)

( * ) Notice: Under 35 U.S.C. 154(b), the term of this patent shall be extended for 0 days.

(21) Appl. No.: 09/024,878

(22) Filed: Feb. 17, 1998

Related U.S. Application Data

(63) Continuation of application No. 08/621,601, filed on Mar. 26, 1996, now abandoned.

(51) Int. Cl.[7] .................................................. A61K 35/78
(52) U.S. Cl. .................. 424/195.1; 424/451; 424/456; 424/464; 424/489; 424/405
(58) Field of Search ................... 424/195.1, 451, 424/456, 464, 489, 405

(56) References Cited

U.S. PATENT DOCUMENTS

| | | |
|---|---|---|
| 3,843,788 | 10/1974 | Iwasa et al. . |
| 4,150,123 | 4/1979 | Szturma . |
| 4,339,442 | 7/1982 | Takemoto et al. . |
| 4,455,298 | 6/1984 | McFarlane et al. . |
| 4,732,760 | 3/1988 | Iga et al. . |
| 4,855,284 | 8/1989 | Emoedi . |
| 4,888,417 * | 12/1989 | Shiraga et al. .................... 536/4.1 |
| 4,913,909 | 4/1990 | Hara et al. . |
| 4,957,741 | 9/1990 | Kamarei et al. . |
| 5,053,498 | 10/1991 | Shiraga et al. . |
| 5,066,496 | 11/1991 | Szabo et al. . |
| 5,080,900 | 1/1992 | Stanley . |
| 5,102,916 | 4/1992 | Antoun . |
| 5,130,133 | 7/1992 | Rajagopalan et al. . |
| 5,176,913 | 1/1993 | Honerlagen et al. . |
| 5,405,608 | 4/1995 | Xu . |
| 5,455,033 | 10/1995 | Silverman et al. . |
| 5,464,620 | 11/1995 | Zhao . |
| 5,466,453 | 11/1995 | Uchida et al. . |
| 5,560,912 | 10/1996 | Neeman et al. . |

FOREIGN PATENT DOCUMENTS

| | | |
|---|---|---|
| 6087757 * | 3/1994 | (JP) . |
| 7242560 * | 9/1995 | (JP) . |

OTHER PUBLICATIONS

Graham et al. Am. J. Gastroenterol. vol. 94/5, pp. 1200–1202, abstract enclosed., 1999.*

Martin J. Blaser. The Bacteria Behind Ulcers. Scientific American, Feb. 1996, pp. 104–107.

* cited by examiner

*Primary Examiner*—Christopher Tate
(74) *Attorney, Agent, or Firm*—Parsons Behle & Latimer

(57) ABSTRACT

The present invention is an orally-administrable composition for preventing and treating *Helicobacter pylori*-associated stomach gastritis and ulcers, and for preventing *Helicobacter pylori*-associated stomach cancer. The invention is a herb or herb extract containing an anti-*H. pylori* activity. The invention further includes methods for making and methods for using the invention.

6 Claims, No Drawings

COMPOSITION AND METHOD FOR TREATING AND PREVENTING *HELICOBACTOR-PYLORI*-ASSOCIATED STOMACH GASTRITIS, ULCERS AND CANCER

CONTINUITY

This application is a continuation of U.S. patent application Ser. No. 08/621,601, filed Mar. 26, 1996, now abandoned.

I. BACKGROUND OF THE INVENTION

A. Field of the Invention

This invention relates to the field of compositions and methods for treating and preventing *Helicobactor pylori*-associated stomach gastritis, ulcers and cancer. More specifically, this invention relates to the field of compositions of herbs, herb parts or herb extracts which can be used to treat or prevent *Helicobactor pylori*-associated stomach gastritis, ulcers and cancer, and methods for making and using such compositions.

B. Description of Related Art

Twelve years ago it was first reported and subsequently verified by many scientific studies that a particular bacterium known as *Helicobacter pylori* ("H. pylori") commonly infects the human stomach. Many people so infected subsequently acquire what is known as chronic superficial gastritis ("stomach inflammation") which may continue on for many decades. It is now known that left untreated, this condition may lead to stomach ulcers and even stomach cancer disease. (Marshall, B. J. and Warren, J. B. Unidentified curved bacilli in the stomach of patients with gastritis and peptic ulceration. *Lancet*, No.8390: 1311–1315 (1984); Nomura, A., Stemmermann, G. N., Chyou, P.-H., et al., *Helicobacter pylori* infection and gastric carcinoma among Japanese Americans in Hawaii. *New Engl. J. Med.*, 325: 1132–1136 (1991); Blaser, M. J. and Parsonnet, J., Parasitism by the "slow" bacterium Helicobacter leads to altered gastric homeostasis and neoplasia. *J. Clin, Invest.*, 94: 4–8 (1994).) Extensive laboratory as well as clinical studies have been reported which clearly show that people suffering from chronic gastritis and/or stomach ulcer disease caused by *H. pylori* infection can be cured when administered certain antibiotics which eradicate *H. pylori* [Rubinstein, G., Dunkin, K. and Howard, A. J., The susceptibility of *Helicobacter pylori* to 12 antimicrobial agents, omeprazole and bismuth salts. *J. Antimicrob. Chemother.*, 34: 409–413 (1994); Rosioru, C. Glassman, M. S., Berezin, S. H., et al., Treatment of *Helicobacter pylori*—associated gastroduodenal disease in children. *Dig. Dis. Sci.*, 38: 123–128 (1993); Blaser, M. J., The bacteria behind the ulcers. *Sci. Amer.*, February 1996, 104–107]. On the other hand, the use of antibiotics has some drawbacks, including the rapid resistance of *H. pylori* to antimicrobial agents (Rubinstein, G. et al., op. cit.) as well as the well known fact that many people are allergic to antibiotics and some develop severe diarrhea and/or secondary infections which complicate antibiotic therapy. Furthermore, the antibiotics used to treat (i.e., kill *H. pylori*) ulcers also kill a wide variety of non-pathogenic bacteria in the body, a most undesirable feature of antibiotic therapy (i.e., "non-selectivity").

II. SUMMARY OF THE INVENTION

The present invention is based on the unexpected discovery that several herbs and an insect product are capable of being orally administered to humans, either singly or in combination, to destroy or inhibit the growth of *H. pylori* so that gastritis and ulcer disease can be prevented or cured. In this manner stomach cancer can also be prevented. The composition may also be combined with certain other beneficial and healing substances (i.e., licorice root (*Glycyrrhiza glabra*)).

The present invention provides the additional benefit that these herbs specifically affect *H. pylori* and not other bacteria normally found in humans. A second advantage of the invention is that these herbs may be used at the same time with standard antibiotics employed to treat ulcer disease without adversely affecting the beneficial and positive effects of such antibiotics.

These and other objects, features and advantages of the invention will be clear to a person of ordinary skill in the art upon reading this specification in light of the appended drawings.

IV. DETAILED DESCRIPTION OF A PREFERRED EMBODIMENT

The present invention is based on the unexpected discovery that several herbs are capable of being orally administered to humans, either singly or in combination, to destroy or inhibit the growth of *H. pylori* so that gastritis and ulcer disease can be prevented or cured and so that stomach cancer can be prevented. The herbs contain an anti-*Helicobacter pylori* activity which reduces the growth rate, survival rate or proliferative ability of *H. pylori*. The herbs may be administered to humans as an oral dosage form alone or in combination with food. The anti-*H. pylori* activity may be effective in treating or preventing disease in all parts of a mammalian digestive tract including, but not limited to, the esophagus, stomach and duodenum. In the most preferred embodiment of the invention, the anti-*H. pylori* activity will be effective at preventing or treating stomach gastritis or ulcers, and in the prevention of stomach cancer.

Composition of the Invention

The herbs of the present invention, which contain an anti-*H. pylori* activity, may be administered in the form of one or more herbs, including herb parts such as leaves, stems, barks, roots, flowers and seeds. In the preferred embodiment of the invention, the herb is one of the herbs identified in Table 1. The herb is preferably ground or powdered to form part of an oral dosage form.

In a more preferred embodiment of the invention, the anti-*H. pylori* activity is isolated from one or more herbs as a dried extract. The extract may be formed by mixing coarsely ground or powdered herb with an extraction solution. Suitable extraction solutions may include water, a buffered aqueous solution, an aqueous alcohol or pure alcohol. In a more preferred embodiment of the invention, the extraction solution is a aqueous alcohol solution comprising from 0 to 100% water and from 0% to 100% pure alcohol by volume. Suitable alcohols include ethanol and methanol. Glycerin may be added as a co-solvent and to stabilize the extract. In the most preferred embodiment of the invention, the extraction solution is 50% aqueous ethanol.

The anti-*H. pylori* activity may be extracted from the herb by any suitable extraction method including, but not limited to, by percolation and by using a mechanical mixer. In either method, the herb is preferably exhaustively extracted to form a concentrated extraction solution. Extraction may be performed from about 20° C. to about 50° C. and beyond. After extraction is complete, the solution is evaporated to form a dried extract. Alternatively, the alcohol may be evaporated from the extraction solution to form an aqueous extract. If dried extracts are formed, the ratio of extract to starting material is generally about 1:5, although greater and lesser yields are within the scope of the invention.

Orally-administrable dosage forms of the invention may include, but are not limited to, capsules, tablets, powders and liquids (hereinafter referred to as "oral dosage forms"). Oral dosage forms may contain one or more herbs or herb extracts. In a preferred embodiment of the invention, an oral dosage from contains from about 10 to about 400 mg total weight of herb or herb extract. In the most preferred embodiment, the oral dosage will contain about 100 mg each of one or more herbs or herb extracts. If a liquid extract is used, the liquid extract can be calibrated by determining the amount of dried extract contained in a given volume of liquid extract. The herb or herb extract may be mixed with inert carriers such that the total activity of the composition can be adjusted. Suitable inert carriers may include inter alia maltodextrin, beet root fiber and tomato fiber.

The composition may further include additional beneficial substances, such as a licorice extract. In a preferred embodiment of the invention, the licorice extract is a deglycyrrhizinated extract.

The extracts containing anti-*H. pylori* activity may beneficially also be admixed with various inactive excipients, carriers, diluents, lubricants and other so-called "pharmaceutical aids" (adjuvants) and then formed into capsules and tablets. Examples of inactive excipients, carriers, diluents, lubricants, disintegrants, and so-called "pharmaceutical aids" include but are not limited to the following: silica, silica gel, cellulose and microcrystalline cellulose, crosscarmelose sodium, dicalcium phosphate, various gums (such as acacia, tragacanth, guar, and xanthan), alginic acid, sodium alginate, corn syrup solids, rice syrup solids, maltodextrin, hydroxypropylcellulose, hydroxypropylmethyl cellulose, corn and potato starches and other plant starches, modified potato starch, stearins, stearic acid, carboxymethyl cellulose, sodium carboxymethyl cellulose, dextrose, fructose, bone meal, oyster shell, isolated soy protein, potassium carbonate, sodium starch glycolate, sorbitol, talc, methylcellulose, polyethylene glycol 400 and other polyethylene glycols, sorbic acid and potassium sorbate, sodium lauryl sulfate, sodium phosphate monobasic, sodium sulfate, potassium bicarbonate, mannitol, lactose, corn flower, zinc gluconate, zinc oxide, xylitol, calcium silicate, sodium ascorbate, citric acid, calcium carbonate, carnauba wax, oils (natural, partial or fully hydrogenated, such as olive oil, peanut oil, cottonseed oil, rape-seed oil, corn oil), magnesium stearate and plant fibers including, but not limited to, beet root fiber and tomato fiber. Additional inactive excipients, carriers, diluents, lubricants and adjuvants which may be used with the enzyme composition are disclosed in Remington's Pharmaceutical Sciences, Ed. 18 (A. R. Gennaro, ed., Mack Publishing Co., Easton, Pa., 1990) and in the Handbook of Pharmaceutical Excipients, Ed. 2 (A. Wade and P. J. Weller, eds., American Pharmaceutical Association, Washington, D.C., and the Pharmaceutical Press, London Publishers, 1994), both of which are incorporated by reference herein in their entirety.

The total amount of herb, extract, carriers, excipients, diluents, lubricants and other so-called "pharmaceutical aids" included in an oral dosage form may be varied according to the preferred size of the oral dosage form. For capsules, the total weight may range from about 275 mg to about 400 mg, although greater or lesser capsule weights are within the scope of the invention. For tablets, the total weight may range from about 400 to about 450 mg, although greater or lesser weights are within the scope of the invention.

METHOD OF MAKING ORAL DOSAGE FORMS

The oral dosage form may include tablets, capsules, powders and liquids. Other equivalent oral dosage forms are within the scope of the invention, as will be readily appreciated by those of skill in the art.

For the manufacture of capsules, tablets (formed into tablets by direct compression only) and powders, it is suitable to mix the appropriate amounts of the herb(s) and or herb extract(s) alone or with required adjuvants, followed by mixing in a blender or other suitable mixing equipment to afford a homogeneous and powdered free flowing mixture which can then be encapsulated or tableted using suitable equipment. Encapsulation and tableting procedures are well-known to those of skill in the art. These procedures are also disclosed in Remington's Pharmaceutical Sciences, Ed. 18, op cit. (especially pages 1615–1675) and in the Handbook of Pharmaceutical Excipients, Ed. 2, op cit., both of which are incorporated by reference herein in their entirety.

For the manufacture of tablets using a wet granulation process, the mixture may be combined, wet-granulated, dried and suitably ground to the desired particle size. The resultant mixture may then be ground and/or mixed using suitable equipment to afford a homogeneous mixture which is then conveniently pressed into tablets of the desired weight and shape using suitable equipment.

Wet granulation processes for tableting are well-known to those of skill in the art. These procedures are also disclosed in Remington's Pharmaceutical Sciences, Ed. 18, op cit., and in the Handbook of Pharmaceutical Excipients, Ed. 2, op cit, which are incorporated by reference herein in their entirety.

Powdered forms of the composition will prepared according to the same procedures which are used for capsules, except that the powder will not be encapsulated. Powdered forms may also be prepared by grinding tablets.

METHOD OF USING THE ENZYME COMPOSITION

The composition of the present invention may be taken alone or in combination with food or liquids. In the preferred embodiment of the invention, the composition is preferably taken with a meal or with liquid. Generally from 1 to 2 oral doses may be taken in form 1 to 4 or more times a day. Powdered forms of the invention may be consumed by dissolving or suspending the powder in water or other suitable beverage.

BEST MODE AND EXAMPLES OF COMPOSITIONS

The following examples include embodiments within the scope of the invention, although the invention is not intended to be limited by or to these embodiments. These examples illustrate preferred embodiments and the best mode of the invention contemplated by the inventor.

BEST MODE

EXAMPLE 1

Capsule
per capsule:

| | |
|---|---|
| Cloves extract (bud) (sorgum aromaticum) | 100 mg |
| Pau d'Arco extract (inner bark) | 100 mg |
| Inula racemosa extract (root) | 100 mg |
| Deglycyrrhizinated licorice extract (root) | 100 mg |
| Capsule Excipient | as needed |

The required amount (scale-up) of the prepared and mixed formulation is used to fill gelatin capsules using suitable equipment, as is readily known to those of skill in the art.

Directions: take 1–2 capsules 3–4 times daily as needed.

PREFERRED EMBODIMENTS

EXAMPLE 2

Tablets
per tablet:

| | |
|---|---|
| Cloves, powdered (bud) | 200 mg |
| Pau d'Arco, powdered (inner bark) | 200 mg |
| Inula racemosa, powdered (root) | 200 mg |
| Licorice root, powdered | 200 mg |
| Tablet Excipient | as needed |

The required amount (scale-up) of the prepared and mixed above formulation is pressed directly into tablets (for example, 7/16" standard round) using suitable equipment, which is known to those of skill in the art.

Directions: take 1–2 tablets, swallowed or chewed, 3–4 times daily, as needed.

EXAMPLE 3

Bulk Powdered Formula
per teaspoon:

| | |
|---|---|
| Cloves Extract (bud) | 100 mg |
| Pau d'Arco extract (inner bark) | 100 mg |
| Inula racemosa extract (root) | 100 mg |
| Deglycyrrhizinated licorice extract (root) | 100 mg |

Bulk Powder Excipient—a sufficient quantity such that each teaspoonful of final product contains 100 mg of each active ingredient.

Directions: mix 1–2 teaspoonsful in 6–8 ounces of liquid (milk, juice, water) and drink 3–4 times daily.

EXAMPLE 4

Capsules
per capsule:

| | |
|---|---|
| Elecampane extract (root) | 100 mg |
| Golden Seal extract (root) | 100 mg |
| Inula racemosa extract (root) | 100 mg |
| Deglycyrrhizinated licorice extract (root) | 100 mg |
| Capsule Excipient | as needed |

The required amount (scale-up) of the prepared and mixed formulation is used to fill gelatin capsules using suitable equipment, as is readily known to those of skill in the art.

Directions: take 1–2 capsules 3–4 times daily as needed.

EXAMPLE 5

Tablets
per tablet:

| | |
|---|---|
| Elecampane, powdered (root) | 200 mg |
| Golden Seal, powdered (root) | 200 mg |
| Inula racemosa, powdered (root) | 200 mg |
| Licorice extract (root) | 200 mg |
| Tablet Excipient | as needed |

The required amount (scale-up) of the prepared and mixed above formulation is pressed directly into tablets (for example, 7/16" standard round) using suitable equipment, which is known to those of skill in the art.

Directions: take 1–2 tablets, swallowed or chewed, 3–4 times daily, as needed.

EXAMPLE 6

Bulk Powdered Form
per teaspoon:

| | |
|---|---|
| Elecampane extract (root) | 100 mg |
| Golden Seal extract (root) | 100 mg |
| Inula racemosa extract (root) | 100 mg |
| Deglycyrrhizinated licorice extract (root) | 100 mg |

Bulk Powder Excipient—a sufficient quantity such that each teaspoonful of final product contains 100 mg of each active ingredient.

Directions: mix 1–2 teaspoonsful in 6–8 ounces of liquid (milk, juice, water) and drink 3–4 times daily.

EXAMPLE 7

Capsules
per capsule:

| | |
|---|---|
| Elecampane extract (root) | 100 mg |
| Bee propolis | 100 mg |
| Golden Seal extract (root) | 100 mg |

-continued

| | |
|---|---|
| Deglycyrrhizinated licorice extract (root) | 100 mg |
| Capsule Excipient | as needed |

The required amount (scale-up) of the prepared and mixed formulation is used to fill gelatin capsules using suitable equipment, as is readily known to those of skill in the art.

Directions: take 1–2 capsules 3–4 times daily as needed.

EXPERIMENTAL DATA

Experiment 1

Objective

To discover natural products capable of exhibiting a high degree of inhibitory activity against the bacterium *H. pylori*, the direct cause of stomach ulcers and eventually certain types of stomach cancer disease.

Methods and Materials

A stock culture of *H. pylori* (ATCC 43504) was used, maintained and employed to streak lawns onto Tryptic Soy Blood Agar (TSBA) according to previously reported methods and protocols [Ansorg, R., von Recklinghausen, G.,Pomarius, R. and Schmid, E. N. Evaluation of techniques for isolation, subcultivation and preservation of *Helicobacter pylori*. *J. Clin. Microb.*, 29: 51–53 (1991)] Briefly, this involved first streaking the TSBA plates with a bacterial suspension and then applying to these plated dried, sterile, filter paper disks previously impregnated with suitably prepared aqueous-alcoholic extracts prepared from a total of 331 different natural substances (i.e., herbs and insects). These disk-containing plates were nest incubated for 48 hours in a high humidity, $CO_2$ incubator receiving a continuous flow of mixed gases to provide an environment of 5–12% carbon dioxide ($CO_2$), 5% oxygen ($O_2$), with the remainder of the environment comprising nitrogen ($N_2$). At the end of the incubation period the disks were examined for antimicrobial activity which was evidenced by a zone of "no growth" (="zone of inhibition") surrounding certain disks. Zones of inhibition were measured (mm) across from one edge of the zone of inhibition to the opposite edge of the zone. Zones of inhibition measuring greater than 18 mm in diameter were considered to represent "active, anti-*H. pylori* activities."

Results and Conclusions

The results for some selected, very active herbs (i.e., "top 21") are shown in table 1, although a total of 55 herbs (and 1 insect derived substance) were found to be active against *H. pylori*.

Experiment 2

Objective

To determine if active anti-*H. pylori* herbs will kill other gram-positive, and gram-negative bacteria normally found in humans.

Materials and Methods

Standard cultures of *Escherichia coli* (*E. coli*), a gram-negative bacteria and *Staphylococcus aureus* (*S. aureus*), a gram-positive bacteria were used to streak agar plates as described previously for *H. pylori* Filter paper disks impregnated with the 55 substances previously found to be active against *H. pylori* were tested for anti *S. aureus* and anti *E. coli* activity on the basis of observing (zones of) inhibition as described previously.

Results and Conclusions

Most of the top 21, most active herbs gave minimal or no activity results against *S. aureus* and *E. coli* (see Table 2). These results strongly suggest that the administration of these herbs to humans will not lead to excessive and undue destruction of other human bacteria which OTHERWISE can often result in most undesirable diarrhea and/or so-called secondary suprainfections.

Experiment 3

Objective

To determine if any of the top 21 most active anti-*H. pylori* natural products interfere with three different standard antibiotics (tetracycline, ampicillin and clarithromycin) which are currently used to treat *H. pylori* ulcer disease.

Materials and Methods

Standard antibiotic test disks containing either tetracycline, ampicillin or clarithromycin were tested for antimicrobial activity against *H. pylori* using the methods described under Experiment 1. At the same time in parallel experiments, each of the top 21 most active anti-*H. pylori* herbs (extracts) was added to individual anti biotic test disks (i.e., each extract was added to a separate disk containing either tetracycline, ampicillin of clarithromycin) and these disks were tested also against *H. pylori*. At the end of the incubation times, the zones of inhibition for the three antibiotics alone versus the zones of inhibition for each antibiotic treated with each of the 21 active herbs were compared.

Interference by an herb(s) was indicated if the zone of inhibition for the disk(s) containing antibiotic plus herb was found to be less than the zone(s) observed for the disk containing antibiotic alone (i.e. no herb).

Results and Conclusions

As expected, all three antibiotics showed antimicrobial activity against *H. pylori*. But, most importantly, NONE of the 21 active anti-*H. pylori* herbs exhibited any inhibitory effect on any of the three active antibiotics tested. This suggests that all of the 21 active anti-*H. pylori* herbal materials could be used advantageously in humans who might be receiving standard antibiotic therapy, at the same time, stated differently any of the 21 anti-*H. pylori* herbs can be used as supportive and/or additional therapy against *H. pylori* at the same time that standard antibiotic therapy is employed in *H. pylori* ulcer disease.

TABLE 1

The top 21, most active Anti-*H. pylori* Natural products

| Common Name | Scientific Name | Part Used | Zone of Inhibition (average of 5 determinations) |
|---|---|---|---|
| Elecampane | *Inula helenium* | root | 39 |
| Pistacia gall | *Pistachia integerrima* | gall | 35 |
| Haritaki | *Terminalia chebula* | fruit | 33 |
| Pau d'Arco | *Tabebuia avellanedae* or *T. altissima* | inner bark | 32 |
| Kutaj | *Holarrhena antidysenterica* | bark | 28 |
| Inula | *Inula racemosa* | root | 28 |
| Bee Propolis (Bee Glue) | Collected by bees from poplars, pines and other trees | resinous material from pines and other trees | 28 |
| Amalaki | *Phyllanthus emblica* | fruit | 28 |
| Bibhitaki | *Terminalia belerica* | fruit | 28 |
| Cloves | *Syzygium aromaticum* | bud | 27 |
| Golden Seal | *Hydrastis canadensis* | root | 27 |
| Yerba Santa | *Eriodictyon californicum* | leaf | 26 |
| Eucalyptus | *Eucalyptus globulus* | leaf | 26 |
| Fever Few | *Tanacetum parthenium* | leaf | 25 |
| Fringe Tree | *Chionanthus virginicus* | root bark | 24 |
| Uva Ursi | *Arctostaphylos uva-ursi* | leaf | 23 |
| Meadow Sweet | *Filipendula ulmaria* | whole plant | 23 |
| Turkey rhubarb | *Rheum officinale* | root | 23 |
| Euphorbia | *Euphorbia hirta* | whole plant | 22 |
| Prickley Ash | *Aanthoxylum americanus* | bark | 21 |
| Black Tea | *Camelia sinensis* | leaf | 21 |

TABLE 2

*E. coli* and *S. aureus* Antimicrobial activity of the top 21 most active anti-*H. pylori* natural substances

| Common Name | *E. coli* | *S. aureus* |
|---|---|---|
| Elecampane | —** | — |
| Pistacia gall | vs* | vs |
| Haritaki | — | vs |
| Pau d'Arco | — | — |
| Kutaj | — | — |
| Inula | — | — |
| Bee Propolis (Bee Glue) | — | vs |
| Amalaki | — | — |
| Bibhitaki | — | — |
| Cloves | — | — |
| Golden Seal | — | vs |
| Yerba Santa | — | vs |
| Eucalyptus | — | — |
| Fever Few | — | — |
| Fringe Tree | — | vs |
| Uva Ursi | — | — |
| Meadow Sweet | — | — |
| Turkey rhubarb | — | — |
| Euphorbia | — | vs |
| Prickley Ash | — | — |
| Black Tea | — | — |

*no zones greater than 10 mm
**no zones of inhibition

I claim:

1. A method for inhibiting *Helicobacter pylori* in mammals, comprising:

orally administering to a mammal a composition comprising between about 10 mg to about 400 mg of powdered herbal parts from Pau d'Arco, *Inula racemosa* and cloves, or aqueous-alcoholic extracts thereof, said composition having an anti-*Helicobacter pylori* activity.

2. The method of claim 1, wherein said composition is an oral dosage form selected from the group consisting of a tablet, a capsule, a powder and a liquid.

3. The method of claim 1, wherein said composition comprises between about 100 mg and about 200 mg of the powdered herbal parts or aqueous-alcoholic extracts thereof.

4. The method of claim 1, wherein said composition further comprises licorice root extract.

5. The method of claim 1, wherein said composition further comprises deglycyrrihizinated licorice extract.

6. A method for inhibiting *Helicobacter pylori* in mammals comprising orally administering a composition comprising between about 10 mg to about 400 mg of powdered Pau d'Arco (*Tabebuia avellandae*) inner bark, powdered *Inula racemosa* root, and powdered clove (*Syzyzyium aromaticum*) buds, or aqueous-alcoholic extracts thereof, said composition having anti-*Helicobacter pylori* activity that is useful to prevent and treat stomach ulcers, gastritis and stomach cancer in mammals.

\* \* \* \* \*